United States Patent [19]

He et al.

[11] Patent Number: 5,746,946
[45] Date of Patent: May 5, 1998

[54] IMIDAZOLIDINONE DERIVATIVES AS CORROSION INHIBITORS

[75] Inventors: Zhigiang Alex He, Ridgefield; Werner Joseph Blank, Wilton, both of Conn.

[73] Assignee: King Idustries, Inc., Norwalk, Conn.

[21] Appl. No.: 774,696

[22] Filed: Dec. 26, 1996

Related U.S. Application Data

[63] Continuation of Ser. No. 391,973, Feb. 21, 1995, abandoned.

[51] Int. Cl.$^6$ .............................. C23F 11/12; C23F 11/14
[52] U.S. Cl. .................. 252/392; 252/394; 422/16; 508/243; 508/244; 508/255; 508/256; 508/259; 508/260; 508/261; 544/316; 544/318; 548/314.7; 548/324.8
[58] Field of Search ..................... 252/392, 394; 422/16; 508/243, 244, 255, 256, 261, 259, 260

[56] References Cited

U.S. PATENT DOCUMENTS

| | | |
|---|---|---|
| 2,613,212 | 10/1952 | Hurwitz et al. . |
| 2,868,727 | 1/1959 | Hughes .................. 507/243 |
| 2,881,155 | 4/1959 | Hankins . |
| 3,312,619 | 4/1967 | Vineyard ............... 548/314.7 |
| 3,350,363 | 10/1967 | Hurwitz . |
| 3,369,008 | 2/1968 | Hurwitz ................. 260/80.72 |
| 4,104,220 | 8/1978 | Sims ...................... 260/29.6 |
| 4,105,417 | 8/1978 | Coon et al. . |
| 4,111,877 | 9/1978 | Dixon et al. . |
| 4,151,142 | 4/1979 | Herman et al. . |
| 4,314,067 | 2/1982 | Herman et al. . |
| 4,340,743 | 7/1982 | Sandri et al. . |
| 4,487,940 | 12/1984 | Sekmakas et al. . |
| 4,491,527 | 1/1985 | Lange et al. . |
| 4,599,417 | 7/1986 | Sekmakas et al. . |
| 4,617,364 | 10/1986 | Sekmakas et al. . |
| 4,632,957 | 12/1986 | Welsh et al. . |
| 4,643,837 | 2/1987 | Zimzik ................... 252/49.3 |
| 4,777,265 | 10/1988 | Merger et al. ........ 548/324.1 |
| 5,066,688 | 11/1991 | Chung et al. . |
| 5,112,984 | 5/1992 | Richey, Jr. et al. . |

FOREIGN PATENT DOCUMENTS

| | | |
|---|---|---|
| 1178578 | 11/1984 | Canada . |
| 2120594 | 10/1994 | Canada . |
| 0272903 | 6/1988 | European Pat. Off. . |
| 0 476 779 A2 | 3/1992 | European Pat. Off. . |
| 0 619 309 A1 | 10/1994 | European Pat. Off. . |
| 1458336 | 1/1967 | France . |
| 3109826 | 9/1982 | Germany . |
| 2131239 | 5/1990 | Japan . |
| 1110009 | 4/1968 | United Kingdom . |
| 1174850 | 12/1969 | United Kingdom . |

OTHER PUBLICATIONS

J. Polymer Sci. Part A: Polymer, Chem. (1986) vol. 24, No. 12 as abstracted by Chemical Abstract 1987:156881.

FR 1458336 (Nov. 10, 1966) as Abstracted by Chemical Abstract 1967:454127.

*Primary Examiner*—Sharon Gibson
*Assistant Examiner*—Valerie Fee
*Attorney, Agent, or Firm*—Morgan & Finnegan, L.L.P.

[57] ABSTRACT

The invention relates to imidazolidinone derivatives formed from the reaction of (1) a substituted-ethyl imidazolidinone; (2) substituted ethyl/propyl propylene urea or (3) a cyclic propylene urea with: (a) a $C_1$–$C_{24}$ alkyl or a $C_3$–$C_{24}$ alkenyl substituted anhydride or, (b) a $C_3$–$C_{24}$ carboxylic acid or corresponding ester; their compositions and use as corrosion inhibitors and/or surfactants.

26 Claims, No Drawings

IMIDAZOLIDINONE DERIVATIVES AS CORROSION INHIBITORS

This is a continuation of application Ser. No. 08/391,973, filed on Feb. 21, 1995, now abandoned.

FIELD OF THE INVENTION

This present invention relates to a novel class of organic compounds, compositions, their preparation and use. The organic compounds of the present invention are imidazolidinone (also known as ethyleneurea, or ureido, or cyclized urea) derivatives having the formula,

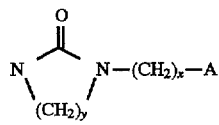 (I)

wherein A is defined as,

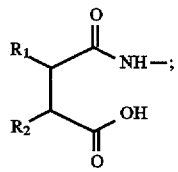 (II)

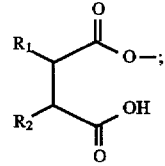 (III)

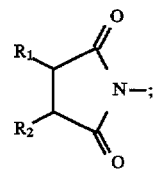 (IV)

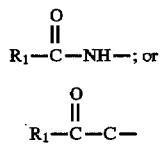 (V)

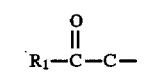 (VI)

and $R_1$ can be H, an alkyl moiety with a $C_1$ to $C_{24}$ chain length or an alkenyl moiety with a $C_3$ to $C_{24}$ chain length; $R_2$ can be H; or $R_2$ and $R_1$ together form a cyclic or aromatic moiety selected from tetra or hexahydrobenzene, alkyl substituted tetra or hexahydrobenzene, or carboxyl substituted benzene; y can be 2 or 3; and x can be 1 to 10.

The imidazolidinone derivatives of the present invention function as high performance corrosion inhibitors and can be used with water treatment, lubricant, grease and coating compositions.

BACKGROUND OF THE INVENTION

Traditional high performance corrosion inhibitors are used in water treatment applications, metal cutting fluids and as rust inhibitors for protective coatings. Typical compounds include lead, chromate and nitrite components and their use have been restricted by new environmental regulations due to their toxicity. As a result, alternatives must be found that provide high anti-corrosive efficiency and low toxicity.

In the past some imidazolidinone derivatives have been used in environments where they provide anticorrosive properties. For example, in Japanese Patent 02-131239, a photoresist remover composition containing 1,3-dimethyl-2-imidazolidinone is used to provide corrosion resistance for Ni, Al and polyimide substrates. In European Patent EP 272903, 1,3-dimethyl-2-imidazolidinone is used as a solvent in a polyarylene sulfide manufacture process to reduce corrosion and in Japanese Patent 62-250043, a magnetic rubber composition containing substituted ethylene thiourea or imidazolidinones provide corrosion resistance for a copper plate. Further, in Japanese Patent No. 55-047385, an imidazolidinone is used as an additive in a corrosion inhibitor composition containing predominantly sodium nitrite (sodium nitrite/imidazolidinone=90/10).

However, imidazolidinone derivatives having vinyl functionality have been used as wet adhesion promoters in latex coatings. See U.S. Pat. Nos. 2,881,155, 3,350,363, 411,877, 4,340,743, 4,617,364, 4,487,940, 4,599,417, 4,314,067, 4,151,142, 4,104,220, 4,632,957, DE 2,732,995 (U.S. Pat. No. 4,111,877) and ZA 7800468. Imidazolidinone derivatives have also been used as a reactive diluent for amino resins (e.g., UCAR® RD 65-2 from Union Carbide or SR-511 from Sartomer) and in electrode position coatings, U.S. Pat. No. 5,066,688. However, these prior art imidazolidinone derivatives were not designed to function as corrosion inhibitors.

Imidazolidinone derivatives having detergent qualities are also known and are used to remove deposits in lubricants (inhibit "lead paint" deposition) (DE 3,314,957) (U.S. Pat. No. 4,491,527) and fuels U.S. Pat. No. 4,105,417. However, the imidazolidinone detergent derivatives include long aliphatic hydrocarbon chains of 30–400 carbon atoms so that they have good solubility in the lubricants being treated. Monofunctional imidazolidinone derivatives, such as those of DE 3314957 and U.S. Pat. No. 4,105,417, with molecular weights above 1000, are ineffective as corrosion inhibitors.

Thus a need exists for corrosion inhibiting compounds and compositions that have high water/lubricant solubility, hydrolytic stability, thermal stability and low toxicity.

SUMMARY OF THE INVENTION

The present invention provides a novel class of organic compounds and compositions based on imidazolidinone derivatives having the formula:

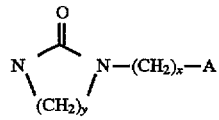 (I)

wherein A is defined as,

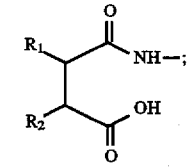 (II)

-continued

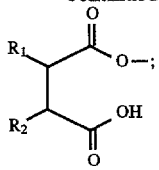 (III)

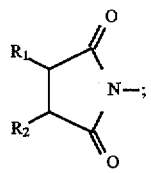 (IV)

 (V)

R₁—C(=O)—NH—; or

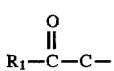 (VI)

R₁—C(=O)—C— and where $R_1$ can be H, an alkyl moiety with a $C_1$ to $C_{24}$ chain length or an alkenyl moiety with a $C_3$ to $C_{24}$ chain length; $R_2$ can be H; or $R_2$ and $R_1$ together form a cyclic or aromatic moiety selected from tetra or hexahydrobenzene, alkyl substituted tetra or hexahydrobenzene, or carboxyl substituted benzene; y can be 2 or 3; and x can be 1 to 10, that possess anti-corrosive and/or surfactant properties, methods of preparing and their use.

An aspect of the present invention is to provide a class of imidazolidinone derivatives that are corrosion inhibitors having anti-corrosive properties and performance equal or superior to corresponding commercial products without the toxicity present in existing commercial products.

A further aspect of the present invention is to provide a class of imidazolidinone derivatives that in addition to their corrosion inhibiting properties have high water/lubricant solubility, hydrolytic stability and thermal stability.

It is an object of the present invention to provide imidazolidinone derivatives that are water soluble and have good hydrolytic stability and contain at least one corrosion inhibitor formed from the reaction of (1) a substituted-ethyl imidazolidinone; (2) a substituted ethyl propyl propylene urea; or (3) a substituted cyclic propylene urea where the substituted moiety is an amino or hydroxy group with a $C_1$–$C_{24}$ alkyl substituted anhydride or a $C_3$–$C_{24}$ alkenyl substituted anhydride.

It is a further object of the present invention to provide imidazolidinone derivatives with good solubility, thermal stability and hydrolytic stability in lubricants.

A still further object of the present invention is to provide imidazolidinone derivatives that inhibit corrosion and are suitable for use in coating and adhesive applications.

It is an object of the present invention to provide imidazolidinone derivative containing compositions for use in water treatment systems, lubricants, and coating and adhesive applications.

These and other object of the present invention will become evident in view of the following description when considered in conjunction with the non-limiting examples. These examples are set forth primarily for illustration and any specific enumeration of detail set forth therein should not be interpreted as a limitation on the case except as is indicated in the appended claims.

DETAILED DESCRIPTION OF THE INVENTION

This invention relates to imidazolidinone derivatives that possess corrosion inhibiting properties and are defined by the formula:

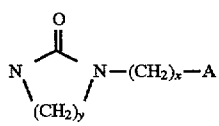 (I)

wherein
A is defined as,

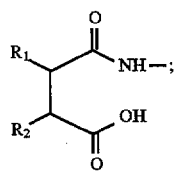 (II)

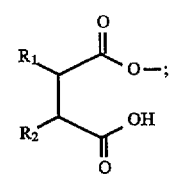 (III)

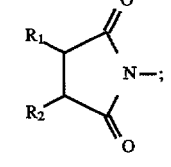 (IV)

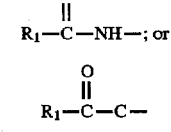 (V)

R₁—C(=O)—NH—; or

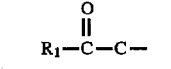 (VI)

R₁—C(=O)—C— and where $R_1$ can be H, an alkyl moiety with a $C_1$ to $C_{24}$ chain length or an alkenyl moiety with a $C_3$ to $C_{24}$ chain length; $R_2$ can be H; or $R_2$ and $R_1$ together form a cyclic or aromatic moiety selected from tetra or hexahydrobenzene, alkyl substituted tetra or hexahydrobenzene, or carboxyl substituted benzene; y can be 2 or 3; and x can be 1 to 10.

The corrosion inhibiting performance of compounds represented by the structures of formulae II–VI above permits their use in water treating systems, metal cutting fluids, and rust inhibitors for protective coatings. When the composition is used to protect metals in aqueous environments such as water, the concentration of the imidazolidinone derivative compounds of the present invention in water can vary from 0.01% to 10% by weight, preferably 0.05% to 2% by weight. Other additives may be also used in the compositions of the present invention to enhance the performance of the compositions, for example, commercial defoamers can be used to reduce the foam formation in the composition. Commercial water based biocides can be used to prevent microorganism attack. The corrosion inhibitors of the present invention may be also used together with other corrosion inhibitors to gain maximum protection. The compounds in the present invention also function as emulsifiers in aqueous solution because of their surfactant nature.

The compound I, when A is a half amide of formula II, was synthesized via chemical modification of 2-aminoethyl imidazolidinone or 3-aminopropyl propylene urea, preferably 2-aminoethyl imidazolidinone, at temperatures below 100° C. The 2-aminoethyl imidazolidinone used in the present invention was synthesized via condensation of diethylenetriamine and urea following the process taught in U.S. Pat. Nos. 2,613,212 and 4,104,220, the subject matter of which are incorporated herein by reference.

Suitable anhydrides used in the present invention include, but are not limited to, phthalic anhydride, trimellitic anhydride, hexahydrophthalic anhydride, methyl hexahydrophthalic anhydride, succinic anhydride, maleic anhydride, (iso-)butenyl succinic anhydride, (iso-)octenyl succinic anhydride, (iso-)nonenyl succinic anhydride, (iso-)decenyl succinic anhydride, (iso-)dodecenyl succinic anhydride, (iso-)hexadecenyl succinic anhydride, (iso-)octadecenyl succinic anhydride, (iso-)eicosenyl succinic anhydride, triacosenyl succinic anhydride, tetracosenyl succinic anhydride, diiso-butenyl succinic anhydride and polyisobutenyl succinic anhydride with average molecular weight up to 435; difunctional and multifunctional anhydrides such as 3,3',4,4'-benzophenonetetracarboxylic dianhydride, 1,2,4,5-benzenetetracarboxylic dianhydride, maleic anhydride based copolymers; or Diels Alder adducts of maleic anhydride and conjugated dienes such as castor oil derivatives, rosin derivatives and cyclopentadiene derivatives. Particularly preferred anhydrides include alkenyl succinic anhydride with the alkenyl moiety having a carbon chain length of from 3 to 24 carbon atoms.

To reduce the viscosity of the reaction mixture, polar solvents, such as water, chloroform, alcohols, n-methyl pyrolidone, etc., may be used. Optionally, tertiary amine neutralizing agents including triethyl amine, pyridine, etc., might be also used. The reaction is exothermic and the temperature of the reaction mixture will rise during mixing process. To avoid imidization by-products, the reaction was run at temperature below 100° C., preferably at 30°–70° C.

The compound I, with A as a half amide of formula II, is soluble in water when it is neutralized with a base. Therefore, the compound is suitable as a high performance corrosion inhibitor in aqueous systems. The base can be an amine, such as triethylamine, triethanolamine, ammonia hydroxide, or metal hydroxides such as, sodium hydroxide or potassium hydroxide. When alkenyl succinic anhydride is used, better water solubility can be obtained when the chain length of the alkenyl moiety contains less than 22 carbon atoms.

The compound I, when A is a half ester of formula III, was synthesized via the reaction of the desired anhydride and 2-hydroxyethyl imidazolidinone or 2-hydroxyethyl propyleneurea or hydroxymethyl imidazolidinone, preferably 2-hydroxyethyl imidazolidinone. The 2-hydroxyethyl imidazolidinone used in this invention is purified from a commercial product (Sartomer SR 511) by azeotropic distillation.

Suitable anhydrides, used to prepare compound I when A is a half ester, include phthalic anhydride, trimellitic anhydride, hexahydrophthalic anhydride, methyl hexahydrophthalic anhydride, succinic anhydride, maleic anhydride, (iso-)butenyl succinic anhydride, (iso-)octenyl succinic anhydride, (iso-)nonenyl succinic anhydride, (iso-)decenyl succinic anhydride, (iso-)dodecenyl succinic anhydride, (iso-)hexadecenyl succinic anhydride, (iso-)octadecenyl succinic anhydride, (iso-)eicosenyl succinic anhydride, triacosenyl succinic anhydride, tetracosenyl succinic anhydride, diiso-butenyl succinic anhydride and polyisobutenyl succinic anhydride with average molecular weight up to 435; difunctional and multifunctional anhydrides such as 3,3',4,4'-benzophenonetetracarboxylic dianhydride, 1,2,4,5-benzenetetracarboxylic dianhydride and maleic anhydride based copolymers; or Diels Alder adducts of maleic anhydride and conjugated diene such as castor oil derivatives, rosin derivatives and cyclopentadiene derivatives. Particularly preferred anhydrides include alkenyl succinic anhydrides with an alkenyl chain length from of 3 to 24 carbon atoms. The reaction can be conducted in an inert organic solvent, such as toluene, xylene, etc. Tertiary amines, such as triethylamine and pyridine, can be used as a catalyst/neutralizing agent.

The compound I, when A is an imide of formula IV, was synthesized by reacting a suitable anhydride and 2-aminoethyl imidazolidinone or 3-aminopropyl propylene urea, preferably 2-aminoethyl imidazolidinone, at temperature above 130° C. The reaction was carried out by heating the mixture of the anhydride and aminoethyl imidazolidinone up to 150° C. for more than 3 hours. Optionally, organic solvents, such as xylene or toluene, may also be used to reduce the viscosity of the mixture and remove the water from the reaction via azeotropic distillation. A water co-product may also be removed via vacuum distillation. Suitable anhydrides used to prepare the imide include phthalic anhydride, trimellitic anhydride, hexahydrophthalic anhydride, methyl hexahydrophthalic anhydride, succinic anhydride, maleic anhydride, (iso-)butenyl succinic anhydride, (iso-)octenyl succinic anhydride, (iso-)nonenyl succinic anhydride, (iso-)decenyl succinic anhydride, (iso-)dodecenyl succinic anhydride, (iso-)hexadecenyl succinic anhydride, (iso-)octadecenyl succinic anhydride, (iso-)eicosenyl succinic anhydride, triacosenyl succinic anhydride, tetracosenyl succinic anhydride, diiso-butenyl succinic anhydride and polyisobutenyl succinic anhydride with average molecular weight up to 435; difunctional and multifunctional anhydrides such as 3,3',4,4'-benzophenonetetracarboxylic dianhydride, 1,2,4,5-benzenetetracarboxylic dianhydride and maleic anhydride based copolymers; or Diels Alder adducts of maleic anhydride and conjugated diene such as castor oil derivatives, rosin derivatives and cyclopentadiene derivatives. Particularly preferred anhydrides include alkenyl succinic anhydride with the alkenyl moiety having 3 to 24 carbon atoms. The imide formation of the products was confirmed by the characteristic absorption in the Fourier transfer infrared (FTIR) spectra of the products.

The compound I, when A is an amide of formula V, was synthesized via the reaction of 2-aminoethyl imidazolidinone or 2-aminoethyl propylene urea, preferably 2-aminoethyl imidazolidinone, and a carboxylic acid or corresponding ester. The carboxylic acid may be any of the carboxylic acids having a $C_3$ to $C_{24}$ chain length, such as 2-ethylhexanoic acid, naphthenic acid, lauric acid, neodecanoic acid, (iso)stearic acid, oleic acid, linoleic acid, castor acid, adipic acid, suberic, azelaic acid, sebacic acid, and etc. The compound may also be obtained by directly reacting 2-aminoethyl imidazolidinone with vegetable oils such as (dehydrated) castor oil, linseed oil, soybean oil, rape seed oil, jojoba oil, cotton seed oil, peanut oil or palm oil.

Compound of formula I, when A is a half ester, an imide, or an amide, is suitable for the use as a high performance corrosion inhibitor in lubricating oil. The compounds according to the present invention may be used 0.01 to 10% by weight, preferably 0.1 to 5% by weight in lubricant. The lubricating oil may be any mineral or non-mineral oil suitable for use as a lubricant. The lubricating oils include, but are not limited to, paraffinic lubricating base stocks of mineral origin, synthetic oils such as poly alpha olefins, e.g. hydrogenated polydecene, synthetic lubricant esters, such as dialkyl adipates and azelates in which the alkyl groups typically have 1 to 20 carbon atoms each, for example, dioctyl azelate, dinonyl adipate or di-(2-ethyl-hexyl)azelate and oils of biological origin including, more particularly, lubricant vegetable oils such as rape seed oil, jojoba oil, cotton seed oil, peanut oil or palm oil. The crude mineral oil may be prepared by either physical separation or chemical conversion or the oil may be a synthetic hydrocarbon base oil.

The lubricating oil can include thickeners to form a grease of suitable thickness, for example, bentonite or hectorite type clay, metal soaps of carboxylic acids such as stearic or 12-hydroxystearic acid, naphthenic acids, rosin oil or tall oil, where the metals are lithium, aluminum, calcium, barium or sodium, or by addition of polyamides or polyureas.

The invention will now be described with reference to the following non-limiting examples.

EXAMPLE 1

Synthesis of 2-aminoethyl imidazolidinone

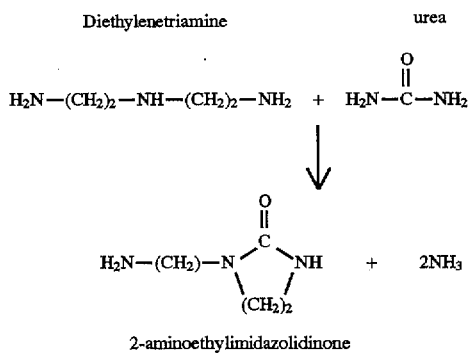

2-aminoethylimidazolidinone

In a suitable reactor equipped with agitation and a reflux condenser, 465 parts by weight of urea and 798 parts by weight of diethylenetriamine were charged. The reaction mix was slowly heated to 140° C. Ammonia started to evolve at about 130° C. The temperature was slowly raised to 150° C. As the evolution of ammonia subsided, vacuum was applied and the remaining ammonia was removed. Product yield was approximately 1000 parts by weight. The product had a viscosity of 6000 cps at 25° C. and an MEQ/g of 6.5. (MEQ=milliequivalent weight). Gel phase analysis of the product showed approximately 95% purity. The product can be used as is or further purified by vacuum distillation. The major impurity is unreacted diethylenetriamine.

EXAMPLE 2

Reaction product of dodecenyl succinic anhydride and 2-aminoethyl imidazolidinone To a solution of 100 parts of triethylamine, 129 parts of product from Example 1 and 205 parts of deionized water in a reactor, 250 parts of dodecenyl succinic anhydride (commercial product from Milliken Chemicals) were added while keeping the reaction temperature below 50° C. After adding all the dodecenyl succinic anhydride, the reaction mixture was continuously stirred for about 5 more hours. The final product is a yellow liquid with a solids content (about 1 hour at about 125° C.) of 58%. The product has a viscosity of 940 cps at 25° C. The FTIR spectrum of a dried sample (film on silver chloride plate dried more than 5 hours in a vacuum oven at room temperature) shows very strong amide absorption at 3295 and 1695 $cm^{-1}$. No characteristic absorption of anhydride groups, at about 1780 and 1730 $cm^{-1}$ was observed.

EXAMPLE 3A–3C

Corrosion inhibition test of product from Example 2

Example 3A

The anticorrosive performance of the product from Example 2 was evaluated by a modified standard test method (ASTM D4627-86). In the test, 1 part of product from Example 2 was neutralized to a pH near 7 with 10% potassium hydroxide and diluted with neutralized deionized water to 100 parts. About 5 grams of cast iron chips were immersed in about 5 grams of the solution in a small petri dish. A clean white filter paper was set underneath the iron chips. After 24 hours, the filter paper was examined for any rust stains. For the filter paper with the solution, absolutely no stains were observed on the paper. The iron chips were visually examined every 24 hours and more fresh deionized water was added from time to time to keep the iron chips covered. After 1000 hours, the iron chips showed no rust. In a comparison test, a control sample without the product from Example 2 showed serious rust within 24 hours.

Example 3B

In another test, 0.09 parts of the product from Example 2 were neutralized with KOH and were diluted with neutralized deionized water to 100 parts. A clean cold rolled steel panel was immersed in this solution. The panel was visually examined every 24 hours for any possible corrosion. After more than 1000 hours, the panel remained clean and showed no corrosion at all. For a comparison, an identical steel panel was immersed in a control solution lacking the product of Example 2 and was corroded after only 3 hours of exposure.

Example 3C

In another test, the corrosion inhibition efficiency of the product from Example 2 was examined in a water borne alkyd bake coatings formulation (Table 1). The coatings were applied to unpolished Bonderite® 1000 iron phosphated cold rolled steel panels (3'×6') and cured at 150° C. for 20 minutes. The thickness of the dried film is 0.2 mils. The dried films were then cross cut and exposed to a corrosive environment in a salt spray chamber. After 1 week of exposure, the distance between the front edge of the corrosion creep and cutting line was recorded for comparison. The results are shown in Table 1. The coating with 1% of the solution from Example 2 showed marked improvement in corrosion resistance compared to the control panels without corrosion inhibitors.

TABLE 1

A WATER BORNE ALKYD BAKE COATINGS FORMULATION AND THE CORROSION RESISTANCE TEST RESULTS

| Component | Control (parts) | Sample (parts) |
|---|---|---|
| Alkyd water reducible[1] | 40.00 | 40.00 |
| HMMM commercial[2] | 10.00 | 10.00 |
| 2-butoxyethanol | 4.00 | 4.00 |
| Dimethylethylamine | 7.88 | 7.88 |
| Silicone flow agent[3] | 0.30 | 0.30 |
| p-Toluene sulfonic acid blocked[4] | 0.64 | 0.64 |
| Product from Ex. 2 | | 1.1 |
| Deionized water | 51.1 | 50.0 |
| Results | | |
| Saltspray ASTM B-117 Creep (mm) | 10+ | 2 |

[1]No. 74-7451 Talloil fatty acid short oil alkyd; Acid number 45–54, 70% in 2-butoxyethanol; Cargill, Inc., P.O. Box 5630, Minneapolis, MN 55440, S
[2]Resimine 747, hexamethoxmethylmelamine; Monsanto Chemical Company, 800 N. Lindbergh Blvd., St. Louis, MO 63167
[3]Byk 301: BYK-Chemie USA, 524 South Cherry Street, Wallingford, CT 06492
[4]NACURE® 2547 amine blocked sulfonic acid; King Industries, Inc., Science Road, Norwalk, CT 06852

EXAMPLE 4

Reaction product of n-octenyl succinic anhydride and 2-aminoethyl imidazolidinone

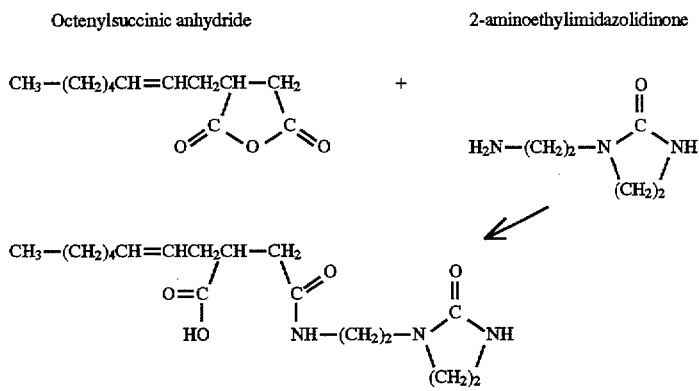

To a reactor containing a solution of 100 parts of triethyl amine, 129 parts of the product from Example 1, 450 parts of chloroform, 210 parts of n-octenyl succinic anhydride (a commercial product from The Humphrey Chemical Company, Inc.) in 300 parts of chloroform were added while keeping the reaction temperature below 50° C. The reaction mixture was stirred for about three more hours at room temperature after the mixing. After the reaction, triethyl amine and chloroform were removed by vacuum distillation. The product is a yellow solid. FTIR spectrum of the product indicates strong absorption of amide at 3295 and 1695 cm$^{-1}$. For the convenience of application, 240 parts of 2-butoxyethanol were added to the solid product to make a solution which has a solids content of 43% (1 hour at 125° C.).

EXAMPLE 5A–C

Corrosion inhibition test of the product from Example 4

Example 5A

The same iron chip test described in Example 3 was used here. 1.4 parts of the solution from Example 4 was neutralized with 10% NaOH and diluted with neutralized deionized water to 100 parts. The iron chips were immersed in this solution and showed no rust for more than 45 days. The filter paper underneath the iron chips showed no rust or stains after 24 hours of exposure.

Example 5B

The corrosion inhibition efficiency of the product from Example 4 was also examined in a water borne alkyd bake coatings formulation (Table 2). The coatings were applied to polished Bonderite® 1000 iron phosphated cold rolled steel panels (3'×6') and cured at 325° F. for about 15 minutes. The thickness of the dried film was 0.5 mils. The dried films were then cross cut and exposed to a corrosive environment in a salt spray chamber. After 500 hours of exposure, the distance between the front edge of the corrosion creep and cutting line was recorded for comparison. The results are shown in Table 2. The coating with 2% of the solution from Example 4 showed better results than the control coatings without any corrosion inhibitors or the comparison coatings using a commercial corrosion inhibitor.

TABLE 2

A WATER BORNE ALKYD BAKE COATINGS FORMULATION AND THE CORROSION RESISTANCE TEST RESULTS

| Component | Control (parts) | Comparison (parts) | Sample (parts) |
|---|---|---|---|
| Alkyd water reducible[1] | 40.00 | 40.00 | 40.00 |
| HMMM commercial grade[2] | 10.00 | 10.00 | 10.00 |
| 2-Butoxyethanol | 4.00 | 4.00 | 4.00 |
| Dimethylethylamine | 7.88 | 7.88 | 7.88 |
| Silicone flow agent[3] | 0.30 | 0.30 | 0.30 |
| p-Toluene sulfonic acid blocked[4] | 0.64 | 0.64 | 0.64 |
| Solution from Example 4 | | | 2.00 |
| Synthetic alkyl naphthalene Zinc sulfonate[5] | | 2.00 | |
| Deionized water | 51.18 | 49.18 | 49.18 |
| Results | | | |
| Saltspray, ASTM B-117 Creep (mm) | 5+ | 5+ | 2 |

[1]No. 74-7451, Talloil fatty acid short oil alkyd; Acid number 47–54, 70% in 2-butoxyethanol; Cargill, Inc., P.O. Box 5630, Minneapolis, MN 55440
[2]Hexamethoxymethylmelamine crosslinker; Monsanto Chemical Company, 800 N. Lindbergh Blvd., St. Louis, MO 63167
[3]BYK-Chemie USA, 524 South Cherry Street, Wallingford, CT 06492
[4]King Industries, Inc., Science Road, Norwalk, CT 06852
[5]A commercial zinc sulfonate corrosion inhibitor

EXAMPLE 6

Reaction product of 2-aminoethyl imidazolidinone and iso-hexadecenyl succinic anhydride

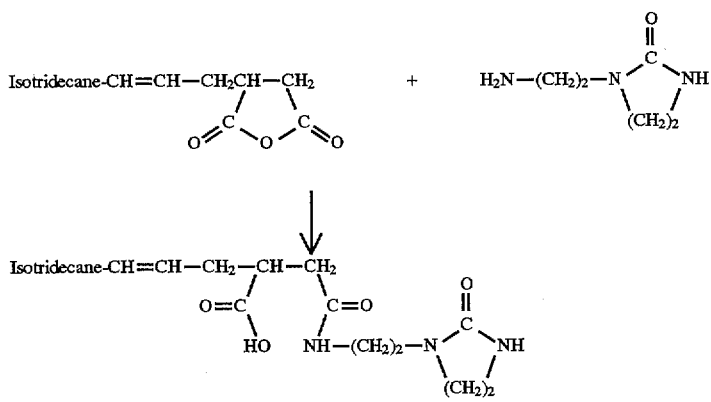

A reaction procedure similar to that of Example 4 was followed where 323 parts of iso-hexadecenyl succinic anhydride (a commercial product from Anhydrides and Chemicals, Inc.) in 150 parts of chloroform were added to a mixture of 100 parts of triethylamine, 129 parts of products from Example 1 and 600 parts of chloroform in a reactor, while keeping the reaction temperature below 50° C. After the addition of the iso-hexadecenyl succinic anhydride, the reaction mixture was stirred for about 3 more hours at 35° C. The triethylamine and chloroform were then removed by vacuum distillation. The product is a yellow solid. The FTIR spectrum of the product supports the amide formation. For the convenience of application, about 450 parts of 2-butoxyethanol were added to dissolve the product and form a product solution. The final solution of the product in 2-butoxyethanol is a yellow liquid with a solids content of 54% (about 1 hour at 125° C.).

EXAMPLE 7

Corrosion inhibition test of the Example 6 produce

The same iron chip test followed in Example 3A and Example 5A was used to test the corrosion inhibition efficiency of the product from Example 6. Specifically, 1.9 parts of the product solution of Example 6 was neutralized with 10% NaOH to a pH near 7.0 and diluted with neutralized deionized water to 100 parts. The iron chips were immersed in this solution and showed no rust for more than 4 days. The filter paper underneath the iron chips showed no rust or stains after 24 hours of exposure.

EXAMPLE 8

Reaction product of 2-hydroxyethyl imidazolidinone and iso-octadecenyl succinic anhydride

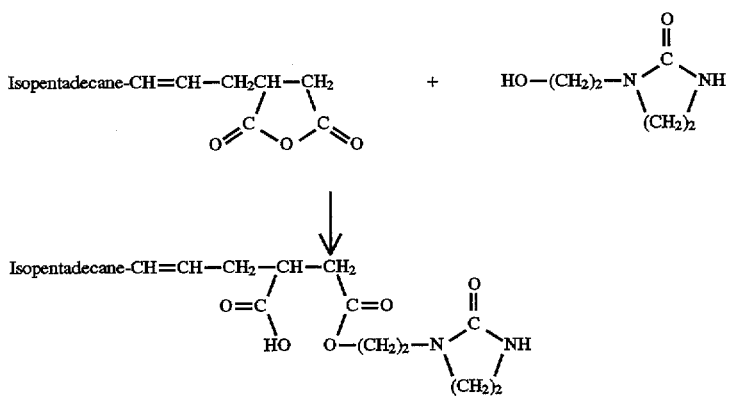

To a solution of 100 parts of triethylamine, 130 parts of 2-hydroxyethyl imidazolidinone and 250 parts of toluene in a reactor, 365 parts of iso-octadecenyl succinic anhydride in 250 parts of toluene at 60° C., in a half hour period, were added. The reflux of the reaction mixture at 78°–80° C. was continued for about 3 more hours. Triethylamine and toluene were then removed via vacuum distillation. The final product is a yellow liquid with viscosity of 6600 cps at 50° C. The infrared spectrum of the product shows strong ester absorption (1734 $cm^{-1}$) and no anhydride absorption (1780 $cm^{-1}$).

EXAMPLE 9

Corrosion inhibition test of the product from Example 8

An ASTM standard test method (D 665 procedure B) was used to examine the corrosion inhibition efficiency of the product from Example 6. In the test, 0.05 parts of the product from Example 6 was diluted with a lubricant (Sunpar LW-110 from Sunoco) to 100 parts. 300 ml of this oil solution was poured into a beaker. A clean cylindrical steel specimen (spindle) was completely immersed in the oil and the oil was stirred for 30 minutes at 60° C. 30 ml of synthetic sea water was added and the oil/water mixture was continuously stirred for 24 hours at 60° C. The specimen was then cleaned with heptane and visually examined. The spindle will pass the test only if there are no kinds of rust or stains on it. The spindle in the solution with 0.05% product from Example 6 passed the test after 24 hour exposure while the control sample in a solution without the product of Example 6 was heavily rusted within 2 hours.

EXAMPLE 10

Reaction product of 2-hydroxyethyl imidazolidinone and dodecenyl succinic anhydride

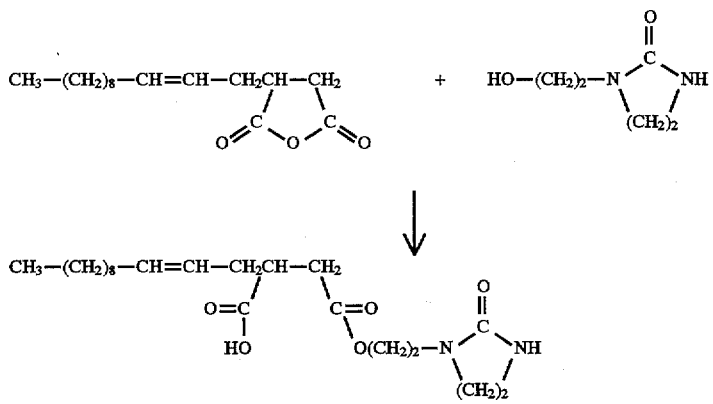

To a solution of 200 parts of triethylamine, 260 parts of 2-hydroxyethyl imidazolidinone and 500 parts of toluene in a reactor, 545 parts of dodecenyl succinic anhydride in 500 parts of toluene at 60° C. in a half hour period were added. The reflux of the reaction mixture at 80° C. was continued for about 3 more hours. Triethylamine and toluene were then removed via vacuum distillation. The final product is a transparent yellowish brown solid. The infrared spectrum of the product shows strong ester absorption (1735 cm$^{-1}$) and no anhydride absorption (1780 cm$^{-1}$).

EXAMPLE 11A–B

Corrosion inhibition test of the product from Example 10

Example 11A

A standard test method for corrosion preventive properties of lubricating greases (ASTM D 1743) was used to test the corrosion inhibiting performance of the product from Example 10. Compositions with concentration of 0.1% and 0.25% by weight of the product from Example 10 were respectively mixed with NLGI #2+lithium 12 OH stearate grease (Witco Corporation, LubriMatic Division, Olathe, Kans., USA). The resulting compositions were tested for anti-corrosion properties using ASTM Test D1743, the standard test method for corrosion preventing properties of lubricating grease. In this test, new, cleaned Timkin roller bearings were packed with the grease to be tested and are then run under a light load for 60 seconds to distribute the grease in a pattern that might be found in service. The bearing were exposed to deionized water and stored for 48 hours at 52±1° C. and 100% relative humidity. After cleaning, the bearing cups were visually examined for evidence of corrosion. The criterion for failure is the presence of any corrosion spot 1.0 mm or longer in the longest dimension. Samples are rated as pass or fail. Both compositions tested passed without any evidence of corrosion.

EXAMPLE 11B

In another test, the product of Example 10 was examined in a high solids coating formulation (Table 3). The coating was applied to unpolished Bonderiteo® 1000 iron phosphated cold rolled steel panels (3'×6') and cured at 120° C. for 20 minutes. The thickness of the dried film was 0.5 mils. The dried films were then cross cut and exposed to corrosion environment in a salt spray chamber. After 90 hours of exposure, the distance between the front edge of the corrosion creep and cutting line was recorded for comparison. The results are shown in Table 3. The coating with 1% of the product from Example 10 showed better results than the control coatings without any corrosion inhibitors.

TABLE 3

A high solids amino bake coatings formulation and the corrosion resistance test results

| Component | Control (parts) | Sample (parts) |
| --- | --- | --- |
| Polyester Polyol[1] | 300.00 | 300.00 |
| HMMM crosslinker[2] | 200.00 | 200.00 |
| Propyl glycol methyl ether acetate | 40.00 | 40.00 |
| Dinonyl naphthalene disulfonic acid blocked[4] | 0.64 | 0.64 |
| Silicone surfactant[3] | 0.16 | 0.16 |
| Product from Example 10 |  | 5.4 |
| Results |  |  |
| Creep (mm) | 5 | 2 |

[1]Cycloaliphatic polyester; MW 450 OH number 230, Viscosity 1000 cps, Nonvolatile >96%; King Industries, Inc., Science Road, Norwalk, CT 06852
[2]Hexamethoxymethylmelamine resin; Monsanto Chemical Company, 800 N. Lindbergh Blvd., St. Louis, MO 63167
[3]Silwet silicone surfactant; Union Carbide, Inc., 39 Old Ridgebury Road, Danbury, CT 06817
[4]Blocked Acid Catalyst, King Ind.

EXAMPLE 12

Higher temperature reaction product of 2-aminoethyl imidazolidinone and iso-octadecenyl succinic anhydride

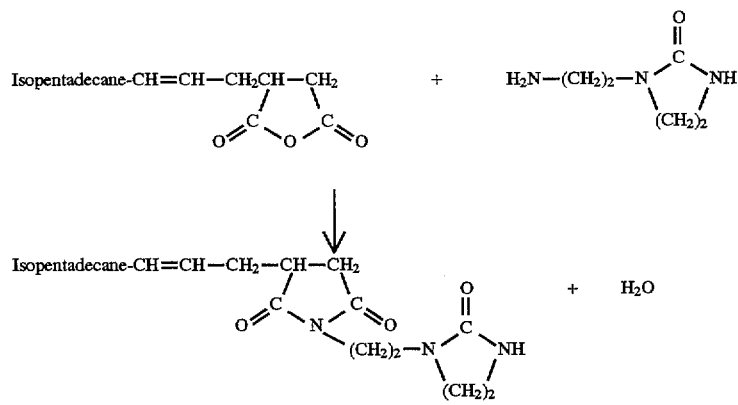

A reactor equipped with a vacuum distillation arm was charged with 387 parts of the product from Example 1, and 998 parts of iso-octadecenyl succinic anhydride, while keeping the reaction temperature at about 100° C. After the addition of the iso-octadecenyl succinic anhydride, the mixture was heated to 150° C. for about 5 more hours with vacuum distillation. The final product is a yellow/brown liquid with a viscosity of 7000 cps at 50° C. The FTIR spectrum of the product shows the characteristic absorption for imide group at 1707 and 1772 cm$^{-1}$.

EXAMPLE 13

Corrosion inhibition test of product from Example 10

The same ASTM standard method of Example 9 was used to test the corrosion inhibition performance of the product from Example 10. Specifically, 0.08 parts of the product from Example 9 were diluted to 100 parts with a mineral lubricant (Sunpar LW-110 from Sunoco). The spindle in this solution passed the test after 24 hours of exposure while the spindle in the control sample, without the corrosion inhibitor product of the present invention, was seriously rusted after only 2 hour exposure.

EXAMPLE 14

Reaction product of methyl oleate and 2-aminoethylimidazolidinone

A mixture of 387 parts of the product from Example 1 and 820 parts of methyl oleate (A commercial product with the trade name Emery 2219 from Henkel Corporation, 11501 Northlake Dr., Cincinnati, Ohio 45249) were introduced into a reactor into which nitrogen was bubbled for 15 min. The mixture was then heated to 200° C. under nitrogen flow. The mixture was continuously stirred for five hours. The product is a yellow wax-type solid at room temperature. The FTIR spectrum of the product shows strong amide absorption at 3306 and 1684 cm$^{-1}$.

EXAMPLE 15

Corrosion inhibition test of the product of Example 14

The product from Example 14 was mixed with NLGI #2+ lithium 12 OH stearate grease (Witco Corporation, Lubri-Matic Division, Olathe, Kans., USA) to form a composition containing a product concentration of 0.25% by weight. The same standard test method for corrosion preventive properties of lubricating greases (ASTM D 1743) of Example 11 was used to test the corrosion inhibiting performance of this composition. The resulting composition tested passed the test.

EXAMPLE 16

Reaction product of a phthalic anhydride with 2-aminoethyl imidazolidinone

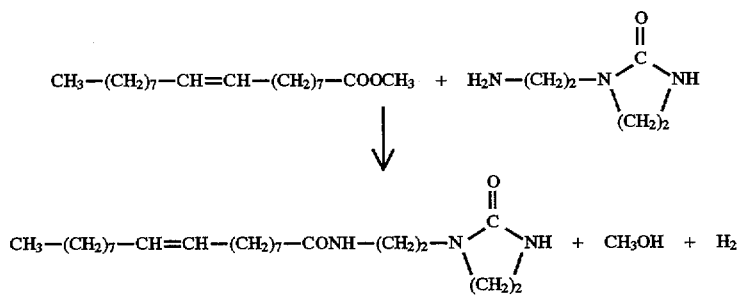

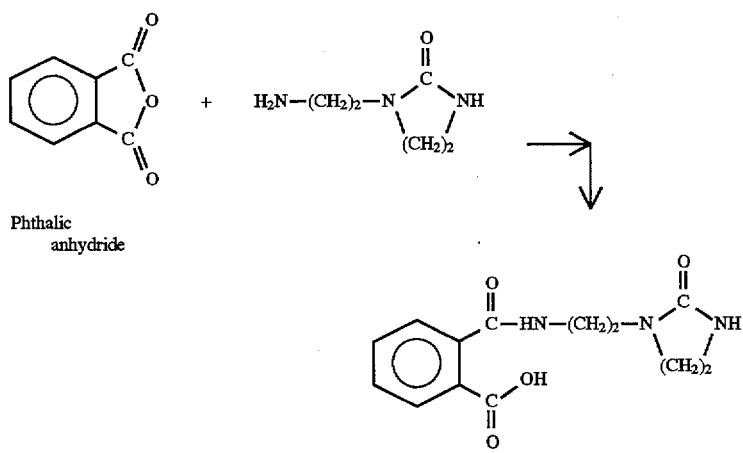

Phthalic anhydride

The same synthetic procedure of Example 4 was followed 100 parts of triethylamine, 129 parts of products from Example 1 and 600 parts of chloroform were mixed with 148 parts of phthalic anhydride in a reactor while keeping the reaction temperature below 50° C. After the addition of phtalic anhydride, the reaction mixture was stirred for about 3 more hours at 35° C. The triethylamine and chloroform were then removed by vacuum distillation. The product is an yellow solid. The FTIR spectrum of the product supports the amide formation. For the convenience of application, about 450 parts of 2-butoxyethanol were added to dissolve the product. The amic acid formed can cyclize to the imide by heating to 150° C. for 3–5 hours.

EXAMPLE 17

(cyclic)

Preparation of a hexahydrophthalic anhydride reaction product with 2-aminoethyl imidazolidinone

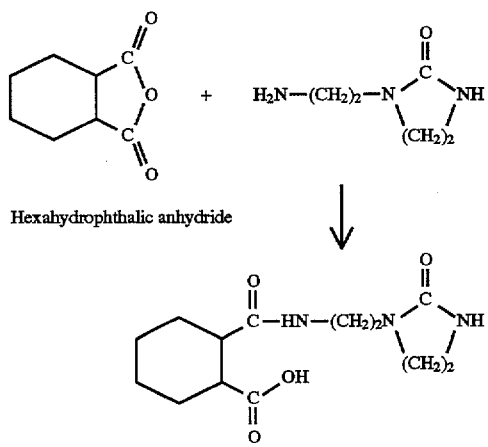

Hexahydrophthalic anhydride

The synthetic procedure of Example 4 was followed to a mixture of 100 parts of triethylamine, 129 parts of products from Example 1 and 600 parts of chloroform in a reactor, 154 parts of hexahydrophthalic anhydride were added while keeping the reaction temperature below 50° C. After the addition, the reaction mixture was stirred for about 3 more hours at 35° C. The triethylamine and chloroform were then removed by vacuum distillation. The product is an yellow solid. The FTIR spectrum of the product supports the amide formation. For the convenience of application, about 450 parts of 2-(butoxyethanol were added to dissolve the product. The amic acid formed can cyclize to the imide by heating to 150° C. for 3–5 hours.

EXAMPLE 18

Preparation of a di substituted derivative with 2-hydroxyethyl imidazolidinone

 + 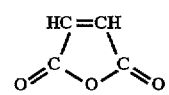

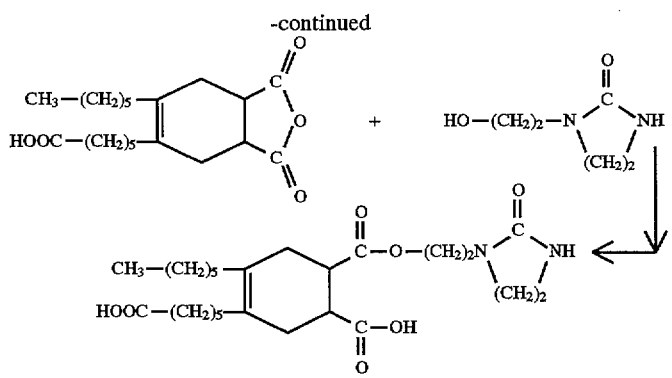

To 280 gram of dehydrated castor oil, 98 gram of maleic anhydride are added. The reaction mixture is heated to 200° C. The maleic anhydride adds to the double bonds of the castor oil by a Diehls-Alder reaction or an α addition. This reaction product is than reacted with 130 gram of 2-hydroxyethyl imidazolidinone. The resulting product is a viscous material with an acid number of 110 and is water dispersible in the presence of an amine. Added to a water-dispersible air-dry alkyd resin at a level of 0.5–3% it reduces creepage in the saltspray test and improves adhesion.

EXAMPLE 19

Reaction product of methylhexahydrophthalic anhydride with 2-amino imidazolidinone

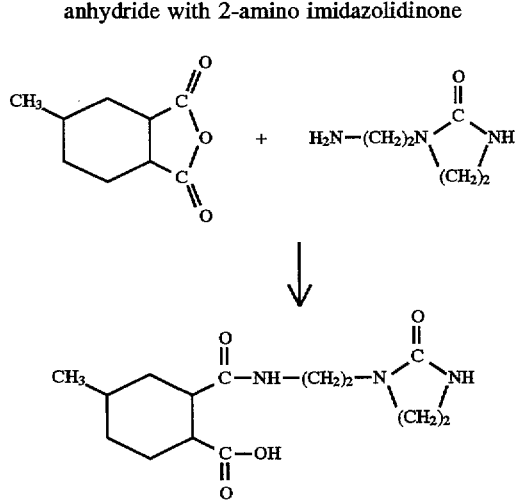

The procedure of Example 4 was followed where, to a mixture of 1 part of triethylamine, 129 parts of products from Example 1 and 600 parts of chloroform in a reactor, 168 parts of methylhexahydrophthalic anhydride while keeping the reaction temperature below 50° C. were added. After the addition, the reaction mixture was stirred for about 3 more hours at 35° C. The triethylamine and chloroform were then removed by vacuum distillation. The product is an yellow solid. The FTIR spectrum of the product supports the acid formation. For the convenience of application, about 450 parts of 2-butoxyethanol were added to dissolve the product.

EXAMPLE 20

Reaction product of 2,3-dimethylmaleic anhydride with 2-aminoethyl imidazolidinone

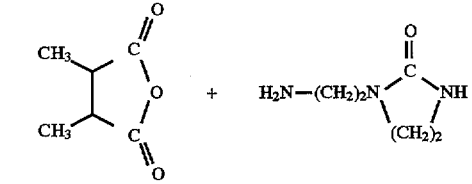

The procedure of Example 4 was followed where, to a mixture of 1 part of triethylamine, 129 parts of products from Example 1 and 600 parts of chloroform in a reactor, 126 parts of 2,3-dimethylmaleic anhydride while keeping the reaction temperature below 50° C. were added. After the addition, the reaction mixture was stirred for about 3 more hours at 35° C. The triethylamine and chloroform were then removed by vacuum distillation. The product is an yellow solid. The FTIR spectrum of the product supports the acid formation. For the convenience of application, about 450 parts of 2-butoxyethanol were added to dissolve the product.

Although the invention has been described in conjunction with the specific embodiments, it is evident that many alternatives and variations will be apparent to those skilled in the art in light of the foregoing description. Accordingly, the invention is intended to embrace all of the alternatives and variations that fall within the spirit and scope of the appended claims. Further, the subject matter of the above cited United States Patents are incorporated herein by reference.

What is claimed is:

1. An imidazolidinone derivative defined by the formula:

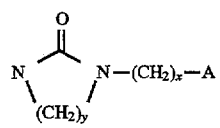  (I)

wherein A is defined as,

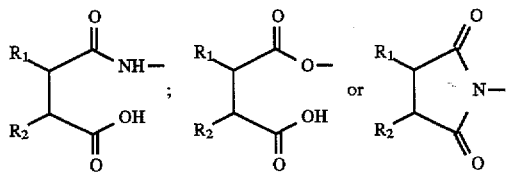

and $R_1$ or $R_2$ is H, an alkyl-moiety with a $C_4$ to $C_{24}$ chain length or an alkenyl moiety with a $C_4$ to $C_{24}$ chain length, or $R_1$ and $R_2$ together form tetra or hexahydrobenzene, an alkyl substituted tetra or hexahydrobenzene, or carboxyl substituted benzene; y is from 2 to 3 and x is from 1 to 10; with the proviso that $R_1$ and $R_2$ are not both hydrogen.

2. A corrosion inhibiting composition including the corrosion inhibitor according to claim 1, where $R_1$ and $R_2$ together form tetra or hexahydrobenzene, alkyl substituted tetra or hexahydrobenzene, or carboxyl substituted benzene.

3. A method of producing a compound according to claim 1 comprising reacting a substituted-ethyl imidazolidinone or (2) a substituted ethyl propylene urea and a $C_4$–$C_{24}$ alkyl substituted anhydride or a $C_4$–$C_{24}$ alkenyl substituted anhydride.

4. A corrosion inhibiting composition including at least one corrosion inhibitor which is formed from the reaction of (1) a substituted-ethyl imidazolidinone or (2) a substituted ethyl propylene urea, and an alkenyl substituted succinic anhydride, said alkenyl substituted anhydride is (iso-)butenyl succinic anhydride, (iso-)octenyl succinic anhydride, (iso-)nonenyl succinic anhydride, (iso-)decenyl succinic anhydride, (iso-)dodecenyl succinic anhydride, (iso-)hexadecenyl succinic anhydride, (iso-)octadecenyl succinic anhydride, (iso-)eicosenyl succinic anhydride, triacosenyl succinic anhydride, tetracosenyl succinic anhydride or diiso-butenyl succinic anhydride.

5. The composition of claim 4, wherein the corrosion inhibitor is formed from the reaction of a substituted ethyl propylene urea and said alkenyl substituted succinic anhydrides.

6. The composition of claim 4, wherein the corrosion inhibitor is formed from the reaction of a substituted ethyl imidazolidinone and said alkenyl substituted succinic anhydride.

7. The composition of claim 4, wherein said substituted ethyl imidazolidinone is 2-hydroxyethyl imidazolidinone or 2-aminoethyl imidazolidinone.

8. The composition of claim 4, wherein said substituted ethyl propylene urea is 2-hydroxyethyl propylene urea or 2-aminoethyl propylene urea.

9. The composition of claim 4, wherein said reaction is conducted at a temperature below 100° C.

10. The composition of claim 4, wherein said reaction is conducted at a temperature above 100° C.

11. The composition of claim 4, wherein dodecenyl succinic anhydride is reacted.

12. The composition of claim 4, wherein n-octenyl succinic anhydride is reacted.

13. The composition of claim 4, wherein iso-hexadecenyl succinic anhydride is reacted.

14. The composition of claim 4, wherein iso-octadecenyl succinic anhydride is reacted.

15. The composition of claim 4, wherein methylhexahydrophthalic anhydride is reacted.

16. The composition of claim 4, wherein hexahydrophthalic anhydride is reacted.

17. A composition comprising an effective corrosion inhibiting amount of an imidazolidinone derivative defined by the formula:

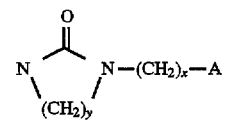  (I)

wherein A is defined as,

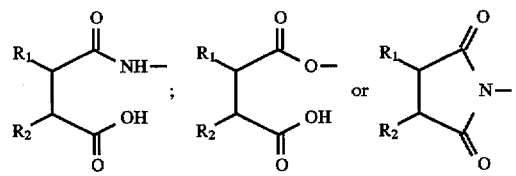

and $R_1$ or $R_2$ is H, an alkyl moiety with a $C_4$ to $C_{24}$ chain length or an alkenyl moiety with a $C_4$ to $C_{24}$ chain length, or $R_1$ and $R_2$ together form tetra or hexahydrobenzene, alkyl substituted tetra or hexahydrobenzene, or carboxyl substituted benzene; y is from 2 to 3 and x is from 1 to 10; with the proviso that $R_1$ and $R_2$ are not both hydrogen.

18. The composition according to claim 17, containing a lubricating oil or grease.

19. The composition according to claim 17, containing a compatible defoaming agent and/or a biocide.

20. A corrosion inhibiting composition including at least one corrosion inhibitor, wherein said at least one corrosion inhibitor is defined by the formula:

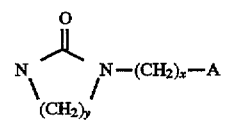  (I)

wherein A is defined as,

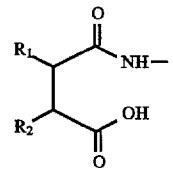

and $R_1$ or $R_2$ is H, an alkyl moiety with a $C_4$ to $C_{24}$ chain length or an alkenyl moiety with a $C_4$ to $C_{24}$ chain length, or $R_1$ and $R_2$ together form tetra or hexahydrobenzene, alkyl substituted tetra or hexahydrobenzene, or carboxyl substituted benzene; y is from 2 to 3 and x is from 1 to 10; with the proviso that RX and $R_2$ are not both hydrogen.

21. A corrosion inhibiting composition including at least one corrosion inhibitor, wherein said at least one corrosion inhibitor is defined by the formula:

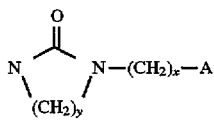

wherein A is defined as,

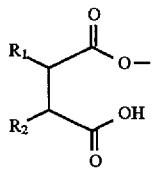

and $R_1$ or $R_2$ is H, an alkyl moiety with a $C_4$ to $C_{24}$ chain length or an alkenyl moiety with a $C_4$ to $C_{24}$ chain length, or $R_1$ and $R_2$ together form tetra or hexahydrobenzene, alkyl substituted tetra or hexahydrobenzene, or carboxyl substituted benzene; y is from 2 to 3 and x is from 1 to 10; with the proviso that $R_1$ and $R_2$ are not both hydrogen.

22. A corrosion inhibiting composition including at least one corrosion inhibitor, wherein said at least one corrosion inhibitor is defined by the formula:

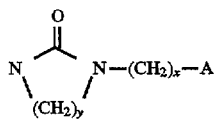
(I)

wherein A is defined as,

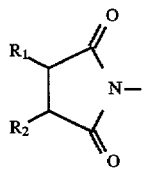
(I)

and $R_1$ or $R_2$ is H, an alkyl moiety with a $C_4$ to $C_{24}$ chain length or an alkenyl moiety with a $C_4$ to $C_{24}$ chain length, or $R_1$ and $R_2$ together form tetra or hexahydrobenzene, alkyl substituted tetra or hexahydrobenzene, or carboxyl substituted benzene; y is from 2 to 3 and x is from 1 to 10; with the proviso that $R_1$ and $R_2$ are not both hydrogen.

23. A method of inhibiting corrosion in aqueous medium comprising adding to an aqueous medium a corrosion inhibiting amount of a compound formed from the reaction of (1) a substituted-ethyl imidazolidinone or (2) a substituted ethyl propylene urea, and a $C_4$–$C_{24}$ alkyl substituted succinic anhydride or a $C_4$–$C_{24}$ alkenyl substituted succinic anhydride.

24. The method of claim 23, wherein said substituted ethyl imidazolidinone is 2-hydroxyethyl imidazolidinone or 2-aminoethyl imidazolidinone.

25. The method of claim 23, wherein said substituted ethyl propyleneurea is 2-hydroxyethyl propylene urea and 2-aminoethyl propylene urea.

26. A method according to claim 23, wherein said reaction is conducted at a temperature below 100° C.

* * * * *

UNITED STATES PATENT AND TRADEMARK OFFICE
CERTIFICATE OF CORRECTION

PATENT NO. : 5,746,946
DATED : May 5, 1998
INVENTOR(S) : He et al.

It is certified that error appears in the above identified patent, and that said Letters Patent is hereby corrected as shown below:

On the title page [75] Inventors: delete "Zhigiang Alex He" and replace with -- Zhiqiang Alex He -- .

| | |
|---|---|
| Col. 1, line 47, | delete "$R_1$-C-C-" and replace with -- $R_1$-C-O- --; |
| line 65, | delete "have" and replace with --has--. |
| Col. 2, line 20, | delete "411, 877" and replace with --4, 111, 877--; |
| line 26, | delete "electrode position" and replace with --electrodeposition--. |
| Col. 3, line 20, | delete "$R_1$-C-C-" and replace with -- $R_1$-C-O- --; |
| line 43, | delete "; or (3) a substituted cyclic propylene urea"; |
| line 56, | delete "object" and replace with --objects--. |
| Col. 4, line 37, | delete "$R_1$-C-C-" and replace with -- $R_1$-C-O- --. |
| Col. 7, line 26, | delete "$H_2$N-($CH_2$)-N" and replace with --$H_2$N($CH_2$)$_2$-N--. |
| Col. 8, line 65, | delete "[4]NACURE®2547amine blocked sulfonic acid; King Industries, Inc., Science Road, Norwalk, CT 06852" and replace with -- [4]NACURE®2547 amine blocked sulfonic acid; King Industries, Inc., Science Road, Norwalk, CT 06852.-- |

UNITED STATES PATENT AND TRADEMARK OFFICE
CERTIFICATE OF CORRECTION

PATENT NO.   : 5,746,946
DATED        : May 5, 1998
INVENTOR(S)  : He et al.

It is certified that error appears in the above identified patent and that said Letters Patent is hereby corrected as shown below:

Col. 11, line 58,   delete "produce" and replace with --product--.

Col. 18, line 32,   delete "2-(butoxyethanol" and replace with --2-butoxyethanol--.

Col. 22, line 64,   delete "RX" and replace with --R₁--.

Signed and Sealed this

First Day of May, 2001

Attest:

NICHOLAS P. GODICI

Attesting Officer    Acting Director of the United States Patent and Trademark Office